US00PP13116P2

(12) United States Plant Patent
Klemm

(10) Patent No.: US PP13,116 P2
(45) Date of Patent: Oct. 22, 2002

(54) CALIBRACHOA PLANT NAMED 'KLEC00072'

(75) Inventor: Nils Klemm, Stuttgart (DE)

(73) Assignee: Klemm & Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 09/904,717

(22) Filed: Jul. 16, 2001

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Annette H. Para
(74) *Attorney, Agent, or Firm*—C. A. Whealy

(57) ABSTRACT

A distinct cultivar of Calibrachoa plant named 'KLEC00072', characterized by its arching and somewhat cascading plant habit; freely branching habit; early and freely flowering habit; relatively large red purple-colored flowers; and good weather tolerance.

1 Drawing Sheet

BOTANICAL CLASSIFICATION

*Calibrachoa sp.* cultivar KLEC00072.

BACKGROUND OF THE INVENTION

The present Invention relates to a new and distinct cultivar of Calibrachoa plant, botanically known as *Calibrachoa sp.*, and hereinafter referred to by the name 'KLEC00072'.

The new Calibrachoa is a product of a planned breeding program conducted by the Inventor in Stuttgart, Germany. The objective of the program is to create new early-flowering Calibrachoa cultivars with cascading and freely branching growth habit and attractive flower colors.

The new Calibrachoa originated from a cross made by the Inventor during the summer of 1998 of a proprietary selection of Calibrachoa identified as code number R 4, not patented, as the female, or seed, parent with a proprietary selection of Calibrachoa identified as code number J 65, not patented, as the male, or pollen, parent. The new Calibrachoa was selected by the Inventor in May, 1999 in a controlled environment in Struttgart, Germany, on the basis of its arching and somewhat cascading plant habit and large red purple-colored flowers.

Asexual reproduction of the new cultivar by terminal cuttings taken in a controlled environment in Stuttgart, Germany since June, 1999, has shown that the unique features of this new Calibrachoa are stable and reproduced true to type in successive generations.

SUMMARY OF THE INVENTION

Plants of the cultivar KLEC00072 have not been observed under all possible environmental conditions. The phenotype may vary somewhat with variations in environment such as temperature, light intensity, daylength, water status and fertility level without, however, any variance in genotype.

The following traits have been repeatedly observed and are determined to be the unique characteristics of 'KLEC00072'. These characteristics in combination distinguish 'KLEC00072' as a new and distinct cultivar of Calibrachoa:

1. Arching and somewhat cascading plant habit.
2. Freely branching habit.

3. Early and freely flowering habit.
4. Relatively large red purple-colored flowers.
5. Good weather tolerance; tolerant to rain and low and high temperatures.

Plants of the new Calibrachoa differed primarily from plants of the female parent selection, R 4, in flower color as flower color of plants of the new Calibrachoa is red purple whereas flower color of plants of the female parent selection is dark red. In addition, plants of the new Calibrachoa are more freely flowering than plants of the female selection. Plants of the new Calibrachoa differ primarily from plants of the male parent selection, J 65, in flower size as plants of the new Calibrachoa have larger flowers than plants of the male parent selection. In addition, plants of the new Calibrachoa have a more upright plant habit than plants of the male selection.

Plants of the new cultivar are similar in flower color to plants of the Calibrachoa cultivar KLEC00073, not patented. However, in side-by-side comparisons conducted by the Inventor in Stuttgart, Germany, plants of the new Calibrachoa differ from plants of the cultivar KLEC00073 in the following characteristics:

1. Plants of the new Calibrachoa are more erect and taller than plants of the KLEC00073.
2. Plants of the new Calibrachoa have larger flowers than plants of the KLEC00073.

BRIEF DESCRIPTION Of THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Calibrachoa. The photograph comprises a close-up view of a typical plant of 'KLEC00072' grown in a hanging basket container.

DETAILED BOTANICAL DESCRIPTION

In the following description, color references are made to The Royal Horticultural Society Colour Chart except where general terms of ordinary dictionary significance are used.

Plants grown in 12-cm containers were used for following description. Plants were grown under conditions which closely approximate commercial production conditions from January to May in Stuttgart, Germany in polyethylene-covered greenhouses. Plants used for the description and the photographs were about four months from planting rooted cuttings. During the production period, day and night temperatures ranged from about 10 to 18° C. and light levels were about 20,000 lux during the beginning of the production period increasing to 50,000 lux towards the end of the production period.

Parentage:

*Female parent*.—Proprietary selection of *Calibrachoa sp.* identified as R 4, not patented.

*Male parent*.—Proprietary selection of *Calibrachoa sp.* identified as J 65, not patented.

Propagation:

*Type cutting*.—Terminal vegetative cuttings.

*Time to initiate and develop roots*.—Summer: About 21 days at 20 to 26° C. Winter: About 28 days at 20° C.

*Root description*.—Numerous, fine, fibrous, well-branched, white in color.

Plant description:

*Form*.—Annual flowering plant; initially upright to semi-upright, arching and somewhat cascading; uniformly mounded appearance.

*Usage*.—Appropriate for hanging baskets, window boxes and patio containers.

*Plant height* (*from soil level to top of plant plane*).—About 10 cm.

*Plant diameter*(*area of spread*).—About 45 cm.

*Growth rate*.—Relatively moderate.

*Branching habit*.—About 5 to 7 lateral branches per plant; pinching is typically not required.

*Lateral branch description*.—Length: About 23 cm. Diameter: About 8 to 12 mm. Internode length: About 5 to 10 mm. Texture: Pubescent. Color: 143B.

*Foliage description*.—Leaves simple, generally symmetrical and long persisting; sessile. Arrangement: Alternate. Length: About 3 to 4 cm. Width: About 8 to 12 mm. Shape: Elliptic. Apex: Acute. Base: Attenuate. Margin: Entire. Texture: Smooth, glabrous. Venation pattern: Pinnate. Color: Young foliage, upper surface: 141A. Young foliage, lower surface: 143A. Mature foliage, upper surface: 137A. Mature foliage, lower surface: 137D. Venation, upper and lower surfaces: 145B.

Flower description:

*Flower type and habit*.—Flowers face somewhat upright or outward; single, axillary; salverform. Flowers not persistent. Very freely flowering with about 10 to 25 flowers per lateral stem. Not fragrant.

*Natural flowering season*.—Spring until frost in the autumn; flowering continous.

*Time to flower*.—Early flowering; plants begin flowering about 11 weeks after planting.

*Flower longevity on the plant*.—About 7 days.

*Flower size*.—Diameter: About 3 to 3.5 cm. Tube length: About 1.7 cm. Throat diameter, distal end: About 9 mm. Tube diameter, proximal end: About 2 mm.

*Flower buds* (*before showing color*).—Length: About 7 mm. Diameter: About 2 to 5 mm. Shape: Roughly oblong. Color: 149C.

*Corolla*.—Arrangement/appearance: Single whorl of five petals, fused into flared trumpet. Petal length from throat: About 1.3 to 1.6 cm. Petal width: About 1.1 to 1.4 cm. Petal shape: Roughly spatulate with obtuse apex. Petal margin: Entire. Petal texture: Smooth, glabrous. Color: Petal, upper surface, when opening: 57A. Petal, lower surface, when opening: 74C. Petal, upper surface, opened flower: 66A, flower color fading to 67A with subsequent development; venation, 71B. Petal, lower surface, opened flower: 64B; venation, 79B. Flower throat (inside): 15B; venation, 187A. Flower tube (outside): 71B; venation, 71B.

*Sepals*.—Arrangement/appearance: Single whorl of five sepals, star-shaped. Length: About 1.8 cm. Width: About 4 mm. Shape: Lanceolate. Apex: Acute. Margin: Entire. Texture: Smooth, glabrous. Color: Upper surface: 138A. Lower surface: 138B.

*Penduncles*.—Length: About 1.6 to 2 cm. Width: About 2 mm. Strength: Moderately strong. Angle: Erect to about 15° from vertical. Texture: Pubescent. Color: 144B.

*Reproductive organs*.—Stamens: Quantity: Five per flower. Anther shape: Elliptic. Anther length: About 1 to 2 mm. Anther color: 11B. Pollen amount: Scarce. Pollen color: 11B. Pistils: Quantity: One per flower. Pistil length: About 9 mm. Stigma shape: Oval. Stigma color: 149A. Style length: About 7 mm. Style color: 150A. Ovary color: 154A.

*Seed*.—Seed production has not been observed.

Disease resistance: Plants of the new Calibrachoa have not been noted to be resistant to Powdery Mildew.

Weather/temperature tolerance: Plants of the new Calibrachoa are tolerant to rain and wind and have been observed to tolerate temperatures from 1 to 45° C.

It is claimed:

1. A new and distinct cultivar of Calibrachoa plant named 'KLEC00072', as illustrated and described.

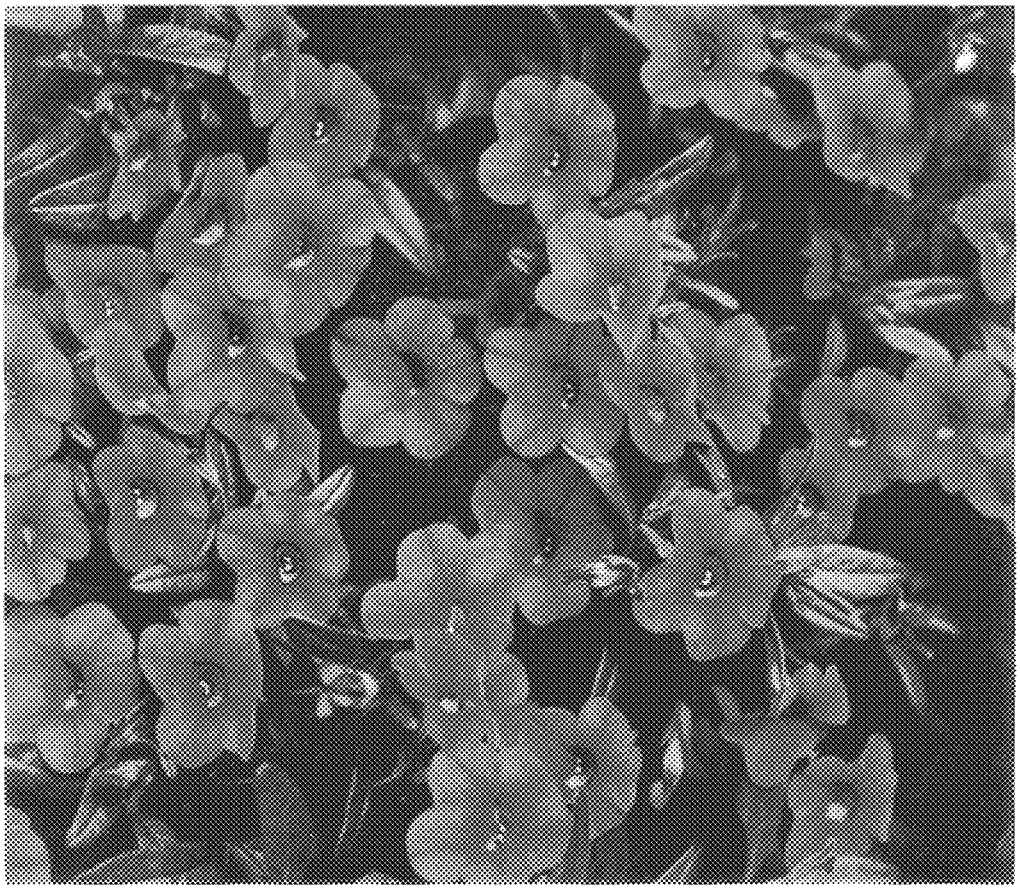

* * * * *